United States Patent [19]

Schinski et al.

[11] Patent Number: 4,531,968
[45] Date of Patent: Jul. 30, 1985

[54] THIOPYRUVIC AMIDE COMPOUNDS

[75] Inventors: William L. Schinski, San Rafael; Raymond J. Lukens, Walnut Creek, both of Calif.

[73] Assignee: Chevron Research Company, San Francisco, Calif.

[21] Appl. No.: 595,225

[22] Filed: Mar. 30, 1984

[51] Int. Cl.$^3$ .................. A01N 9/12; C07C 153/05
[52] U.S. Cl. ........................................ 71/98; 564/74
[58] Field of Search .............................. 564/74; 71/98

[56] References Cited

U.S. PATENT DOCUMENTS

| | | | |
|---|---|---|---|
| 3,879,455 | 4/1975 | Tilles | 71/98 |
| 4,028,409 | 6/1977 | Kramer et al. | 564/74 |
| 4,230,484 | 10/1980 | Batch et al. | 71/98 |

OTHER PUBLICATIONS

Kluger et al., Phosphoenolpyruvamides, Amide-Phosphate Interactions in Analogues of Phosphoenolpyruvate, J. Am. Chem. Soc., 1984, 106 (4017–4020), published Jul. 11, 1984.

*Primary Examiner*—Charles F. Warren
*Assistant Examiner*—Roberta A. Picard
*Attorney, Agent, or Firm*—J. A. Buchanan, Jr.; T. G. De Jonghe

[57] ABSTRACT

Halothiopyruvic amides, which have viricidal and/or fungicidal activity of the formula:

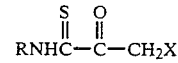

wherein
X is chloro, fluoro, bromo or iodo; and
R is cyclohexyl substituted with 0, 1 or 2 lower alkyl groups, or phenyl substituted with 0, 1 or 2 lower alkyl groups.

6 Claims, No Drawings

THIOPYRUVIC AMIDE COMPOUNDS

FIELD OF THE INVENTION

The present invention relates to certain pyruvic acid amides which have viricidal and/or fungicidal activity.

BACKGROUND OF THE INVENTION

The use of chemical compounds to control fungal diseases of plants is well known.

In contrast, the use of chemical compounds to control viral diseases is not presently done on any large commercial scale. However, certain compounds have been reported as having an antiviral activity, such as certain 2-substituted benzimidazoles against tobacco mosaic virus (TMV), Cassells et al., Z. Naturforsch. C. Biosic, 1982, 37c (5-6) 390-3; poly-(2-methyl-5-virylpyridine N-oxide against TMV, Sugimura et al., J. Agric. Food Chem., 1983 31(3), 665-7; certain thiadiazoles against potato X virus, Schuster et al., East German Pat. No. 157,664, 1982; and certain 3-trihalomethyl-5-ureido-1,2,4-oxadiazoles and -1,2,4-thiadiazoles against southern bean mosaic virus, Gay et al., U.S. Pat. No. 4,353,920, 1982.

Virus diseases of food crops or other plant crops include: tobacco mosaic, cucumber mosaic, bean common mosaic, bean yellow mosaic, and necrotic ring spot of stone fruits (prunus necrotic ring spot virus).

SUMMARY OF THE INVENTION

According to the present invention, compounds of the following formula are provided:

$$\text{RNHC}\overset{\overset{S}{\|}}{-}\overset{\overset{O}{\|}}{C}-CH_2X$$

wherein x is chloro, fluoro, bromo or iodo; and R is cyclohexyl substituted with 0, 1 or 2 lower alkyl groups, or phenyl substituted with 0, 1 or 2 lower alkyl groups. "Lower alkyl groups" is used herein to mean alkyl groups of 1 to 5 carbon atoms.

Preferred compounds in accordance with the present invention are those wherein R is 2,6-dimethylphenyl or cyclohexyl, and X is chloro.

Among other factors, the present invention is based on our finding that the compounds of the present invention have antiviral and/or fungicidal activity. We have found that N-cyclohexyl-2-chloro-thiopyruvamide has substantial antiviral activity, particularly against tobacco mosaic virus and barley stripe mosaic virus.

The compounds can be made by reacting an aryl or cycloalkyl isocyanide in accordance with the Reactions A and B illustrated below. The ring structure attached to the isocyanide can be saturated or unsaturated and substituted or unsubstituted, for example with lower alkyl groups. Preferred reaction conditions are given below in the examples.

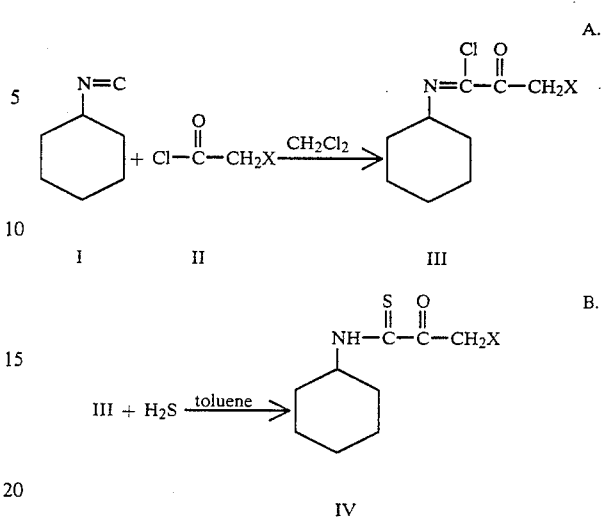

The viricidal compounds of the present invention can be applied to plants in an oil spray or in an aqueous spray. The viricidal compound can also be applied as a soak for plants or plant parts such as seeds, potato seed pieces, and roots.

Adjuvants such as biological inert carriers and wetting agents can be used with the compounds to enhance the viricidal and fungicidal activity, and so that the active compound may be sufficiently diluted in the spray or dust to be applied to the plant or plant part. Usually the active compounds will be used in concentrations of 40 parts per million up to about 5 percent by weight in a suitable carrier. Preferred concentrations are about 0.01 percent to 0.5 percent by weight of active compound in the carrier.

Preferred carriers include a penetrant and a solvent or a solid diluent. Penetrants include dimethylsulfoxide, dimethyl formamide, or N-methyl-2-pyrrolidone. Solvents include cyclohexanol, methyl iso-butyl ketone, alcohols, hydrocarbons, etc. Solid diluents include kaolin, talc, calcium carbonate, Fuller's earth, montmorillinite, diatomaceous earth, starches, sugars, silicas, wood powders and the like.

U.S. Pat. No. 4,353,920, issued Oct. 12, 1982, describes various means of formulating and applying agricultural viricides. The disclosure of U.S. Pat. No. 4,353,920 is incorporated herein by reference.

In addition to enhancement of activity of the viricidal compounds by selection of preferred adjuvants, the compounds of the present invention may be combined with other active ingredients to obtain viricidal activity enhancement.

EXAMPLES

Example 1

N-cyclohexyl-2-chloro-thiopyruvamide Preparation

Chloroacetyl chloride, 11.3 gm, was added to a solution of 10 gm of cyclohexyl isocyanide and 100 ml of methylene chloride at 0° C. The mixture was stirred at room temperature for 7 hours, cooled in an ice bath overnight, and then concentrated under vacuum to give a pale yellow oil. The oil was taken up in 250 ml of toluene and then H₂S was slowly bubbled through the solution for 6 hours. The solution was sealed in a flask and allowed to stand overnight in an ice bath. The solvent was then removed, leaving a dark red oil which was chromatographed on a column of silica gel slurry packed in hexane. Approximately 250 gm of silica gel was used.

After hexane and methylene chloride were eluted from the chromatograph, a red oil was obtained. The red oil crystallized. The red oil was then recrystallized from hexane, giving 4.3 gm of an orange solid. The melting point of the solid was 70°–73° C. The analysis for elemental makeup was as follows:

|   | Calc. | Found |
|---|-------|-------|
| N | 6.37 | 6.73 |
| C | 49.20 | 51.78 |
| H | 6.42 | 7.08 |
| S | 14.59 | — |
| Cl | 16.13 | — |

Example 2

N-2,6-dimethyl-phenyl-2-chloro-thiopyruvamide Preparation

This preparation was carried out similar to the preparation of compound 1 except that the isocyanide used as a starting material was 2,6-dimethylphenyl isocyanide.

Example 3

Control of TMV on Pinto Bean

Table 1 below shows the percent control of tobacco mosaic virus on pinto beans which the compounds of Examples 1 and 2 (referred to herein as Compounds 1 and 2, respectively) gave compared to a standard of nickel nitrate.

TABLE 1

| | Percent Control | | |
|---|---|---|---|
| Concentration, ppm | Compound 1 | Compound 2 | Ni(NO$_3$)$_2$ |
| 250 | 81* | 58** | 57 |
| 100 | 96 | 68 | 52 |
| 40 | 92 | 43 | 34 |

*98 percent on retest
**65 percent on retest

The procedure used in the test was as follows:

Fresh extractions of TMV in 1 percent carborundum were swabbed on leaves of bean seedlings. After 3 hours the inoculated leaves were dipped in an acetone/water solution of the test chemicals. The plants were held 4 to 6 days for lesion development.

Example 4

Barley Stripe Mosaic Virus (BSMV)

Table 2 below shows the reduction of BSMV on Barley seedlings for Compound 1 as compared to controls.

TABLE 2

| Dosage*, ppm | BSMV Symptomatic Plants % Reduction vs Controls |
|---|---|
| 10 | 1.44 |
| 100 | 10.44 |
| 110 | 40.97 |

*Dosage based on uptake on a dry seed basis.

The procedure used in the test was as follows:

Barley seeds 31 percent infested with stripe mosaic were soaked 24 hours in a solution containing Compound 1 and 1 percent dimethylsulfoxide. Seeds were planted in potted soil under greenhouse conditions. The percentage of seedlings showing mosaic symptoms in leaves was determined 2 weeks after the seeds were planted.

Example 5

Fungicidal Activity of Compound 2

Table 3 gives fungicidal data for Compound 2 as compared to captafol, a standard fungicide.

TABLE 3

| | Inhibition of Mycelial Growth ED-99 at ug/cm$^2$ | |
|---|---|---|
| Fungus | Compound 2 | Captafol (Difolatan fungicide) |
| Pythium ultimum | 0.78 | 0.23 |
| Rhizoctonia solani | 0.72 | 0.19 |
| Fusaruim moniforme | 1.23 | 0.62 |
| Botrytis cinerea | 0.97 | 0.69 |
| Aspergillus niger | 1.09 | 0.42 |

Solutions of 0.5 percent a.i. (active ingredient) in acetone/water were atomized onto the agar surface containing mycelial fragments in petri dishes. Threshold inhibitory concentrations were determined from the size of the zones of exhibition of growth.

The efficacy of foliar sprays of Compound 2 on 4 plant diseases are given in Table 4.

TABLE 4

| | Percent Disease Control | |
|---|---|---|
| Plant Disease | Compound 2 (ppm) | Standard (ppm) |
| Tomato late blight | 50(250) | 18(16) Mancozeb |
| Celery late blight | 0(250) | 75(100) Difolatan |
| Bean powdery mildew | 0(250) | 99(16) Karathane |

Solutions of 0.25 percent a.i. in acetone/water were applied to foliage of potted plants. The spore inoculum was sprayed onto the respective plants 1 day following treatment with the 0.25 percent a.i. solution, except for bean rust in which case the inoculum was applied 2 days prior to treatment. Percent leaf area covered with disease was estimated 1 to 2 weeks after inoculation for the several diseases.

What is claimed is:

1. A compound of the formula:

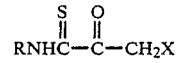

wherein
X is chloro, fluoro, bromo or iodo; and
R is cyclohexyl substituted with 0, 1 or 2 lower alkyl groups, or phenyl substituted with 0, 1 or 2 lower alkyl groups.

2. A compound in accordance with claim 1 wherein R is phenyl.

3. A compound in accordance with claim 1 wherein R is 2,6-dimethylphenyl and X is chloro.

4. A compound in accordance with claim 1 wherein R is cyclohexyl and X is chloro.

5. A viricidal composition comprising the compound of claim 4 and a biological inert carrier therefor.

6. A method for controlling viral diseases of plants comprising applying to the plants a viricidally effective amount of the compound of claim 4.

* * * * *